(12) United States Patent
Gunday et al.

(10) Patent No.: US 10,349,821 B2
(45) Date of Patent: Jul. 16, 2019

(54) CLEANING SYSTEM FOR MEDICAL IMAGING DEVICE

(75) Inventors: Erhan H. Gunday, Great Neck, NY (US); Lawrence J. Gerrans, San Anselmo, CA (US); Alex Hsia, San Jose, CA (US)

(73) Assignee: Sanovas Intellectual Property, LLC, Reno, NV (US)

( * ) Notice: Subject to any disclaimer, the term of this patent is extended or adjusted under 35 U.S.C. 154(b) by 1211 days.

(21) Appl. No.: 13/480,153

(22) Filed: May 24, 2012

(65) Prior Publication Data

US 2012/0238816 A1    Sep. 20, 2012

Related U.S. Application Data

(63) Continuation-in-part of application No. 13/037,874, filed on Mar. 1, 2011, now Pat. No. 10,058,235.

(51) Int. Cl.
*A61B 1/12*    (2006.01)
*A61B 1/00*    (2006.01)
(Continued)

(52) U.S. Cl.
CPC .......... *A61B 1/126* (2013.01); *A61B 1/00135* (2013.01); *A61B 1/122* (2013.01);
(Continued)

(58) Field of Classification Search
CPC . A61B 1/00142; A61B 1/018; A61B 1/00101; A61B 1/0008; A61B 1/012;
(Continued)

(56) References Cited

U.S. PATENT DOCUMENTS 3,773,034 A    11/1973  Burns et al.
4,685,473 A    8/1987   Karcher et al.
(Continued)

FOREIGN PATENT DOCUMENTS

EP    2111782 A2    10/2009
JP    63246132 A    10/1988
(Continued)

OTHER PUBLICATIONS

International Search Report adn Written Opinion of the International Searching Authority Application No. PCT/US2012/027205 Completed: Aug. 22, 2012; dated Sep. 7, 2012 13 pages.
(Continued)

*Primary Examiner* — John P Leubecker
(74) *Attorney, Agent, or Firm* — Forge IP, PLLC

(57) ABSTRACT

An imaging catheter device includes a catheter body with a proximal end, a distal end, and a lumen; a cleaning member disposed at the distal end; and an imaging device movably disposed in the lumen and through the cleaning member; wherein the cleaning member includes a conduit through which the imaging device moves and a flexible material at least partially occluding the conduit such that the imaging device displaces at least some of the flexible material when moved through the conduit. A method of cleaning an imaging catheter device includes disposing a cleaning member including a conduit and a flexible material at least partially occluding the conduit at a distal end of a catheter lumen; positioning an imaging device in the catheter lumen; and cleaning the imaging device by moving it through the conduit such that it displaces at least some of the flexible material.

29 Claims, 13 Drawing Sheets

US 10,349,821 B2
Page 2

(51) Int. Cl.
    *A61B 90/70* (2016.01)
    *A61M 25/00* (2006.01)

(52) U.S. Cl.
    CPC ............... *A61B 2090/701* (2016.02); *A61M 2025/0019* (2013.01)

(58) Field of Classification Search
    CPC .......... A61B 1/12; A61B 1/015; A61B 1/126; A61B 1/00137; A61B 19/34; A61B 2017/3441; A61B 1/121; A61B 17/3417; A61B 1/00103
    USPC ............... 600/101, 104, 109, 127, 129, 133, 600/153–158; 604/523, 528, 95.01, 604/95.02, 95.04, 95.03
    See application file for complete search history.

(56) References Cited

U.S. PATENT DOCUMENTS

| | | | |
|---|---|---|---|
| 4,890,602 A | 1/1990 | Hake | |
| 4,906,230 A | 3/1990 | Maloney et al. | |
| 4,909,787 A | 3/1990 | Danforth | |
| 4,983,165 A | 1/1991 | Loiterman | |
| 5,037,391 A | 8/1991 | Hammerslag et al. | |
| 5,054,501 A | 10/1991 | Chuttani et al. | |
| 5,308,323 A | 5/1994 | Sogawa et al. | |
| 5,313,934 A | 5/1994 | Wiita et al. | |
| 5,314,428 A | 5/1994 | Marotta | |
| 5,375,589 A * | 12/1994 | Bhatta | 600/104 |
| 5,392,766 A * | 2/1995 | Masterson et al. | 600/157 |
| 5,415,663 A | 5/1995 | Lazarus et al. | |
| 5,471,706 A * | 12/1995 | Wallock et al. | 15/302 |
| 5,619,993 A | 4/1997 | Lee | |
| 5,693,015 A | 12/1997 | Walker et al. | |
| 5,715,817 A | 2/1998 | Stevens-Wright et al. | |
| 5,860,914 A | 1/1999 | Chiba et al. | |
| 5,906,590 A | 5/1999 | Hunjan et al. | |
| 5,916,178 A | 6/1999 | Noone et al. | |
| 6,083,170 A | 7/2000 | Ben-Haim | |
| 6,409,657 B1 | 6/2002 | Kawano | |
| 6,527,732 B1 | 3/2003 | Strauss et al. | |
| 6,543,451 B1 * | 4/2003 | Crump et al. | 128/207.14 |
| 7,608,056 B2 | 10/2009 | Kennedy, II | |
| 7,799,013 B2 | 9/2010 | Gandras | |
| 8,001,984 B2 | 8/2011 | Sasaki | |
| 8,343,041 B2 * | 1/2013 | Byers et al. | 600/154 |
| 2003/0083613 A1 | 5/2003 | Schaer | |
| 2004/0181188 A1 | 9/2004 | Schaer et al. | |
| 2004/0186378 A1 | 9/2004 | Gesswein | |
| 2005/0004433 A1 | 1/2005 | Hirata | |
| 2006/0089535 A1 | 4/2006 | Raz et al. | |
| 2006/0149129 A1 | 7/2006 | Watts et al. | |
| 2007/0060997 A1 | 3/2007 | de Boer | |
| 2007/0083082 A1 | 4/2007 | Kiser et al. | |
| 2007/0100235 A1 | 5/2007 | Kennedy, II | |
| 2007/0282168 A1 * | 12/2007 | Kaye et al. | 600/159 |
| 2007/0282253 A1 * | 12/2007 | Sasaki | 604/93.01 |
| 2008/0051735 A1 * | 2/2008 | Measamer et al. | 604/265 |
| 2008/0147000 A1 | 6/2008 | Seibel et al. | |
| 2008/0251102 A1 * | 10/2008 | Haack et al. | 134/6 |
| 2008/0290605 A1 * | 11/2008 | Brockmeier | A61B 17/3462 277/355 |
| 2009/0030400 A1 | 1/2009 | Bose et al. | |
| 2009/0036733 A1 * | 2/2009 | Wallace et al. | 600/104 |
| 2009/0036886 A1 * | 2/2009 | Utley et al. | 606/41 |
| 2009/0062614 A1 * | 3/2009 | Adzich et al. | 600/129 |
| 2009/0105543 A1 * | 4/2009 | Miller et al. | 600/155 |
| 2009/0178681 A1 * | 7/2009 | Bracken | 128/207.15 |
| 2009/0240111 A1 | 9/2009 | Kessler et al. | |
| 2009/0250081 A1 | 10/2009 | Gordin et al. | |
| 2010/0010437 A1 | 1/2010 | Miles et al. | |
| 2010/0087705 A1 * | 4/2010 | Byers et al. | 600/104 |
| 2010/0168665 A1 | 7/2010 | Skerven | |
| 2011/0092892 A1 * | 4/2011 | Nitsan et al. | 604/28 |
| 2011/0130784 A1 * | 6/2011 | Kusleika | 606/200 |
| 2012/0004507 A1 * | 1/2012 | Kaye | 600/154 |
| 2012/0059448 A1 * | 3/2012 | Parker et al. | 623/1.11 |
| 2012/0285488 A1 * | 11/2012 | Labib et al. | 134/22.12 |
| 2012/0330099 A1 * | 12/2012 | Moreno et al. | 600/109 |
| 2013/0139850 A1 * | 6/2013 | Axelsson et al. | 134/6 |
| 2013/0150670 A1 * | 6/2013 | O'Prey et al. | 600/127 |
| 2013/0171030 A1 * | 7/2013 | Ferlic et al. | 422/119 |
| 2013/0190857 A1 * | 7/2013 | Mitra et al. | 623/1.23 |

FOREIGN PATENT DOCUMENTS

| | | |
|---|---|---|
| JP | 0975302 A | 3/1997 |
| JP | 2006055324 A | 3/2006 |
| JP | 2009513308 A | 6/2008 |
| WO | 9524149 A1 | 9/1995 |
| WO | 2007001217 A1 | 1/2007 |
| WO | 2009054491 A1 | 4/2009 |

OTHER PUBLICATIONS

European Search Report; Application No. EP 12 15 7645; dated Apr. 30, 2012; dated May 8, 2012; 8 pages.

* cited by examiner

CLEANING SYSTEM FOR MEDICAL IMAGING DEVICE

CROSS-REFERENCE TO RELATED APPLICATIONS

The present application is a continuation-in-part of pending U.S. patent application Ser. No. 13/037,874, filed on Mar. 1, 2011, the disclosure of which is incorporated by reference herein in its entirety.

FIELD OF THE INVENTION

This invention generally relates to the field of medical imaging devices. In particular, the present invention relates to a system and method for cleaning a medical imaging device in situ.

BACKGROUND OF THE INVENTION

In general, catheters are used in medical procedures in which tubular structures, lumens, pleural cavities or spaces of the body, such as airways, vessels, organs and joints, are diagnostically examined and/or therapeutically treated. Catheters, which can be introduced into the body through a natural orifice or through an incision, can deliver imaging devices, surgical instruments, implants, fluids, drugs, pharmacologic materials, biologic materials, biologic agents and therapeutics to treat or remedy various pathologies found therein. Catheters also guide and deliver other components, such as guide wires, scaffolds and tools, to the intended site within the body.

Catheters are commonly used with imaging devices to provide direct visualization of bodily cavities for diagnostic and therapeutic purposes. Such imaging catheter systems represent a significant advance in various fields of surgery permitting the performance of the majority of medical procedures through a number of small incisions reducing postoperative pain and enhancing the postoperative recovery. The imaging catheter systems allow a surgeon to perform the procedure through small holes using long instruments and observing the internal anatomy with a visualization device together with the means for illumination, such as incoherent fiber bundle or LED(s).

Flexible, semi-rigid and rigid endoscopes are also widely used in medicine to provide direct visualization for diagnostic and therapeutic purposes. Flexible, semi-rigid and rigid endoscopes are available in many sizes and configurations intended for use in different parts of the body and for a variety of diagnostic and therapeutic procedures. The visualization device (i.e., a fiber optic image bundle or a sensor at the distal tip of the device), together with the means for illumination, are an integral part of the endoscope. Endoscopes may also provide working channels to guide and deliver other instruments to the desired site.

In all medical procedures that employ medical imaging devices, such as imaging catheters or endoscopes, the objective lens and the illumination device of the imaging device often becomes soiled or obscured during operative procedures by fog, blood, other body fluids or tissue particles. Due to the small size of the objective lenses, any droplet of liquid or moisture, or piece of tissue results in a dramatic compromise of the field of view, requiring the surgeon to pause the procedure in order to clean the lenses.

A common prior art approach for dealing with such obscuring of the distal lens has been to remove the imaging device from the patient and to manually clean it. For example, there are commercial cleaning kits available, including a sponge or fabric pad and a bottle of cleaning solution. The surgeon has to remove the imaging device from the patient, soak the sponge with the cleaning solution, clean the imaging device by wiping the distal lens against the sponge, and then reinsert the device into the patient. While this approach works to temporarily clean the imaging device lens, it has apparent disadvantages. The need to withdraw the imaging device from the patient, clean it, reinsert it, and relocate the target is highly inefficient and inconvenient. Furthermore, the entry port into the patient often collects blood or other debris, and once the imaging device is reinserted into the patient after the manual cleaning, the distal lens of the imaging device immediately becomes dirty again. Therefore, just keeping the lens of an imaging device clean enough to enable a particular medical procedure is often quite inconvenient and significantly extends the operative time of the procedure.

There have been a number of attempts to overcome the disadvantages of the above described cleaning systems. For example, it has been proposed to incorporate spray washing systems on a catheter that is used with the imaging device to allow cleaning of a distal lens without removing the imaging device from the patient. Examples of such systems are described in U.S. Pat. No. 5,313,934 to Wiita et al., U.S. Pat. No. 6,409,657 to Kawano, and U.S. Pat. No. 8,001,984 to Sasaki. While these prior art systems are more efficient than the external cleaning systems, they still suffer from a number of drawbacks. Such systems typically require incorporation of at least one additional lumen and associated hardware for the wash system, which further complicates construction of the imaging catheter, making it more expensive and requiring a larger diameter. Additionally, washing of a distal lens by simply spraying it with liquid while the device is in place will not always be effective in cleaning the lens. Furthermore, the requirement of incorporating a washing system in the medical device itself does not permit cleaning of existing medical devices already in use, and requires replacement with models incorporating a wash system, which can be relatively expensive.

Other prior art systems, such as those described in US 2009/0105543 to Miller et al. and US 2009/0250081 to Gordin et al., utilize standalone cleaning devices that are introduced into the surgical area via a secondary port in the patient's abdomen. While such devices may be more effective in cleaning the lens of an imaging device, they require an additional incision and thus are more invasive. Additionally, because a surgeon is required to manipulate the imaging device and the cleaning device at the same time, such cleaning procedures are more complicated and time consuming. Furthermore, such cleaning systems are difficult to use in small bodily cavities/spaces.

What is desired, therefore, is a system and method for cleaning medical imaging devices that is more effective than known systems that employ fluid to clean the lenses of the imaging device. What is also desired is a cleaning system that is more cost effective, disposable, and simpler in design. It is further desired to provide a cleaning system that allows a surgeon to clean the imaging device lenses without the need to remove the device from a patient's body and that can be inserted through the same incision as the imaging device. Yet further, it is desired to provide a cleaning system that can be used with existing medical devices already in use.

SUMMARY OF THE INVENTION

It is an object of the present invention to provide an improved and more effective system and method for cleaning medical imaging devices that overcomes the disadvantages of the prior art systems and methods that employ fluid to clean the imaging device.

It is also an object of the present invention to provide a system and method for cleaning medical imaging devices that allows a surgeon to clean the imaging device lenses without the need to remove the imaging device from a patient's body.

It is a further object of the present invention to provide a system and method for cleaning medical imaging devices that is less invasive and can be inserted through the same incision as the imaging device.

It is a yet further object of the present invention to provide a system and method for cleaning medical imaging devices that is more cost effective and simpler in design, and that can be used with existing medical devices.

It is also the object of the invention to provide a system and method for cleaning medical imaging devices wherein a moisturizing fluid is used to further aid object lens cleaning through the same working channel that is used for the imaging device.

In order to overcome the deficiencies of the prior art and to achieve at least some of the objects and advantages listed, an imaging catheter device is provided including a catheter body with proximal end, a distal end, and a lumen; a cleaning member disposed at the distal end of the catheter body; and an imaging device movably disposed in the lumen and through the cleaning member; wherein the cleaning member includes a conduit through which the imaging device moves; and wherein the cleaning member further includes a flexible material at least partially occluding the conduit such that the imaging device displaces at least some of the flexible material when moved through the conduit to clean said imaging device.

In some embodiments, the cleaning member is removably attached to the distal end of the catheter body.

In certain advantageous embodiments, the cleaning member is movable relative to the imaging device. In other advantageous embodiments, the imaging device is movable relative to the cleaning member.

In certain embodiments, the cleaning member includes a plurality of flexing flaps at least partially occluding the conduit. In some of these embodiments, at least one of the flexing flaps is not aligned with at least one other flexing flap.

In some advantageous embodiments, the flexible material the flexible material is sponge material. In additional advantageous embodiments, the flexible material the flexible material is yarn material.

In certain embodiments, the imaging catheter device further includes a fluid supplied to the cleaning member via the lumen of the catheter body.

A cleaning system for a medical imaging device is also provided, including a housing for positioning at a distal end of the imaging device; and a cleaning member disposed in the housing; wherein the cleaning member includes a conduit through which an imaging device moves; and a flexible material at least partially occluding the conduit such that the imaging device displaces at least some of the flexible material when moved through the conduit.

In some advantageous embodiments, the flexible material is sponge material. In additional advantageous embodiments, the flexible material is yarn material.

In some embodiments, the cleaning member includes a plurality of flexing flaps at least partially occluding the conduit. In certain of these embodiments, the plurality of flexing flaps comprises silicone material. In additional of these embodiments, the plurality of flexing flaps comprises fabric material. In further of these embodiments, at least one of the flexing flaps is not aligned with at least one other flexing flap. In other of these embodiments, the cleaning system further includes at least one spacer element positioned between adjacent flexing flaps. In yet further of these embodiments, each of the plurality of flexing flaps has a different color or texture.

In certain embodiments, a fluid is supplied to the housing. In some of these embodiments, the cleaning member is impregnated with the fluid. In certain of these embodiments, the fluid is saline. In additional of these embodiments, the fluid is alcohol. In yet further of these embodiments, the cleaning member retains the fluid via surface tension.

In additional embodiments, the cleaning system also includes a lumen for supplying the fluid to the housing. In certain of these embodiments, the lumen accommodates the fluid suctioned from the housing.

In some embodiments, an outer diameter of the housing is substantially equal to an outer diameter of the catheter body.

In certain embodiments, a distal end of the housing has a rounded shape. In some embodiments, the distal end of the housing is made with flexible material such that said housing deflects away from bodily structures in a patient's body.

A method of cleaning a medical imaging device is further provided, including the steps of positioning a cleaning member at a distal end of the imaging device, the cleaning member including a conduit and a flexible material at least partially occluding the conduit, and cleaning the imaging device by moving at least one of the imaging device and the cleaning member relative to the other to move the imaging device through the conduit in the cleaning member such that the imaging device displaces at least some of the flexible material.

In certain advantageous embodiments, the cleaning device is moved relative to the imaging device to move the imaging device through the conduit in the cleaning member. In other advantageous embodiments, the imaging device is moved relative to the cleaning member to move the imaging device through the conduit in the cleaning member.

In some embodiments, the method further includes the step of supplying a fluid to the cleaning member via a lumen in the imaging device. In certain of these embodiments, the step of supplying fluid to the cleaning member includes impregnating the flexible material with the fluid.

In some cases, the method further includes the step of suctioning the fluid from the cleaning member via a lumen in the imaging device.

In certain embodiments, the method includes the step of supplying pressurized air to the cleaning member.

In some embodiments, the cleaning member comprises a plurality of flexing flaps at least partially occluding the conduit.

In some advantageous embodiments, the flexible material comprises sponge material. In other advantageous embodiments, the flexible material comprises yarn material.

In certain embodiments, the method further includes repeating the step of moving the imaging device through the conduit in the cleaning member.

Other objects of the invention and its particular features and advantages will become more apparent from consideration of the following drawings and accompanying detailed description.

DETAILED DESCRIPTION OF THE INVENTION

Figure 1:
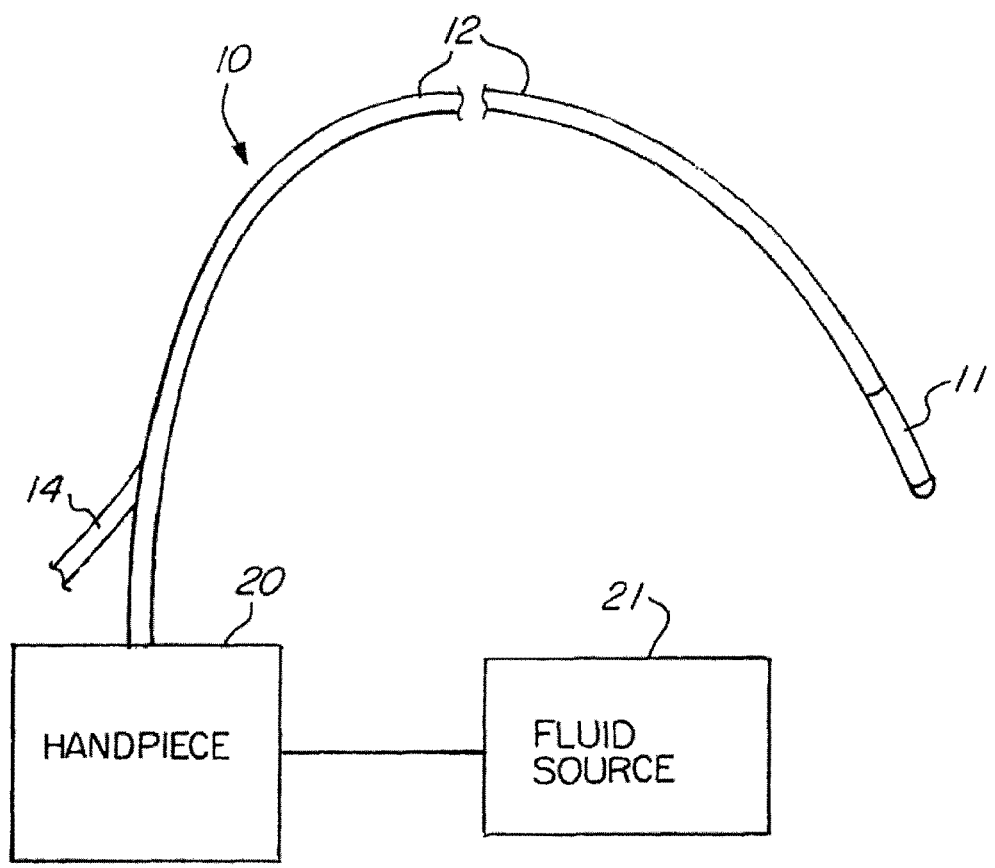
FIG. 1 is a schematic view of an imaging catheter device with a cleaning system in accordance with the present invention.

The basic components of one embodiment of an imaging catheter device with a cleaning system in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The cleaning system of the present invention can be used with various types of imaging devices, such as various guiding catheter devices and endoscopes that include imaging capabilities. In an advantageous embodiment, the cleaning system of the present invention is used with a steerable catheter system described in U.S. patent application Ser. No. 13/037,874, the disclosure of which is incorporated by reference herein in its entirety. The cleaning system of the present invention is low-cost, disposable and simple in design.

FIG. 1 illustrates an exemplary embodiment of an imaging catheter device that utilizes a cleaning system of the present invention. The imaging catheter (10) includes a catheter body (12) having a proximal end (13) and a distal end (15), and an inner lumen (16) extending along a longitudinal axis of the catheter body (12). The imaging catheter (12) may have any suitable diameter and length depending on a particular application, and may be flexible, rigid or semi rigid. The catheter (12) may be made with any commercially available material, such as polyethylene, that is flexible enough to allow the shaft to be safely inserted through the available opening of a bodily cavity such that it will bend instead of puncturing the walls of the cavity, and at the same time is rigid enough such as it will maintain its shape as it is passed alongside and/or through the available opening of the bodily cavity.

The proximal end (13) of the catheter (10) is provided with a handpiece (20) for controlling and manipulation of the catheter by a surgeon. A fluid source (21), such as a pump or a syringe, is also coupled to the distal end of the catheter (10) for supplying fluid to expansion devices that may be provided on the catheter and/or to supply cleansing solution to the cleaning system (11), as will be discussed in more detail below. The catheter (10) also includes a connection port (14) for insertion of an imaging device (not shown). The imaging device is disposed in the inner lumen (16) of the catheter body (12) and extends out of an opening provided at the distal end (15) of the catheter to visualize tissue in front of the catheter. The imaging device may be used to help position the catheter (10) at a proper location inside a patient's body, or to provide an image of a target tissue area for diagnostic purposes or to assist the surgeon during a surgical procedure.

The imaging device can be any device suitable for viewing the target area, such as an optical element and lens assembly having a sufficiently small outer diameter. In some cases, the imaging device has a pre-shaped distal tip that enables it to easily extend through the opening at the distal end of the catheter (10). The distal tip of the imaging device is preferably flexible such that it can be translated linearly or rotationally thereby allowing for 360° visualization of the surrounding area.

The cleaning system (11) is disposed at the distal end (13) of the catheter body (12). In some advantageous embodiments, the cleaning system (11) is removably attached to the distal end of the catheter body (12) by any suitable attachment mechanism, such as a snap-fit or screw-on connection. In other embodiments, the cleaning system (11) may be an integral part of the catheter body (12).

Figure 2:
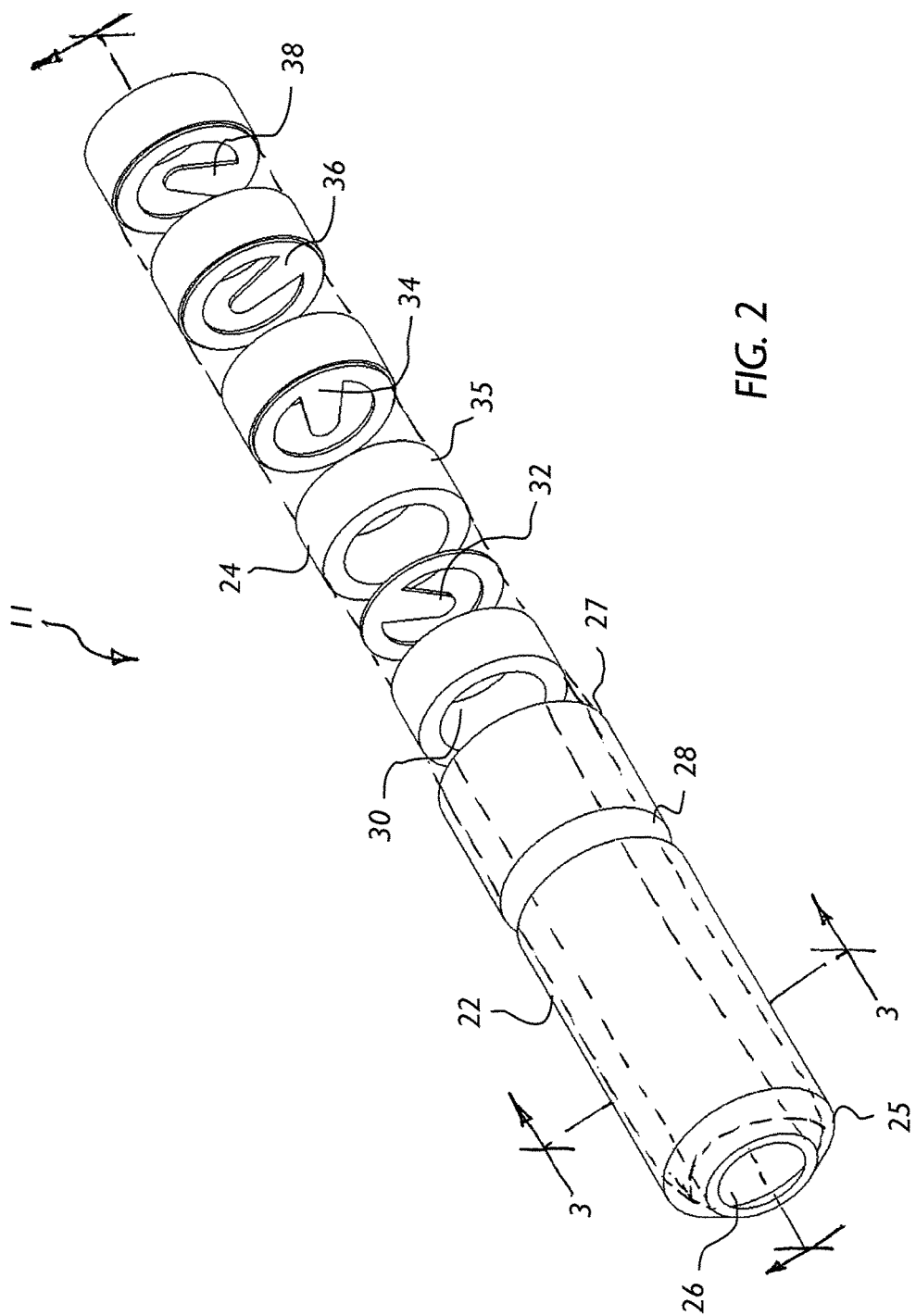
FIG. 2 is an enlarged schematic view of the cleaning system of FIG. 1.

A more detailed view of an exemplary embodiment of the cleaning system (11) is illustrated in FIG. 2. The cleaning system (11) includes an outer housing (22) and a cleaning member (24) disposed within the housing. The housing (22) may be made with any suitable commercially available material that is flexible enough such that, during the insertion of the catheter into a patient's body, it will bend when encountering bodily tissues and/or organs instead of puncturing them. In some embodiments, the housing (22) has a shape similar to the shape of the catheter body and an outer diameter that is substantially the same as the outer diameter of the catheter body. Further, a distal end (25) of the housing (22) preferably has a rounded shape to facilitate a safe and smooth insertion of the catheter into bodily cavities. The rounded distal end (25) of the housing (22) is designed such that it holds in any particles and or pieces of cleaning members (24) that may break loose.

The housing (22) has an opening (26) at its distal end (25). The opening (26) is connected with a conduit (30) provided in the cleaning member (24), which in turn is connected with the lumen of the catheter. When the imaging catheter is in use, the imaging device is inserted into the lumen of the catheter, and is moved through the conduit (30) of the cleaning member (24) and out of the opening (26). The cleaning member includes a flexible material at least partially occluding the conduit (30). Thus, when the imaging device is moved through the cleaning member (24), it displaces at least some of the flexible material and any debris trapped on the lens of the imaging device are thereby wiped off.

In the embodiment shown in FIG. 2, the cleaning member (24) comprises a plurality of flexing flaps (32, 34, 36, 38). Each of the flexing flaps (32, 34, 36, 38) extends into the conduit (30) of the cleaning member (24) and is positioned at a different location around the circumference of the cleaning member, as more clearly shown in a cross-sectional view in FIG. 3. The flexing flaps (32, 34, 36, 38) are preferably made with thin flexible material, such as silicone, fabric, or any other suitable elastomeric or fibrous material. When the imaging device is moved through the conduit (30), the flexing flaps (32, 34, 36, 38) contact the lens of the imaging device, thereby wiping off any debris or residue from the lens.

Figure 3:
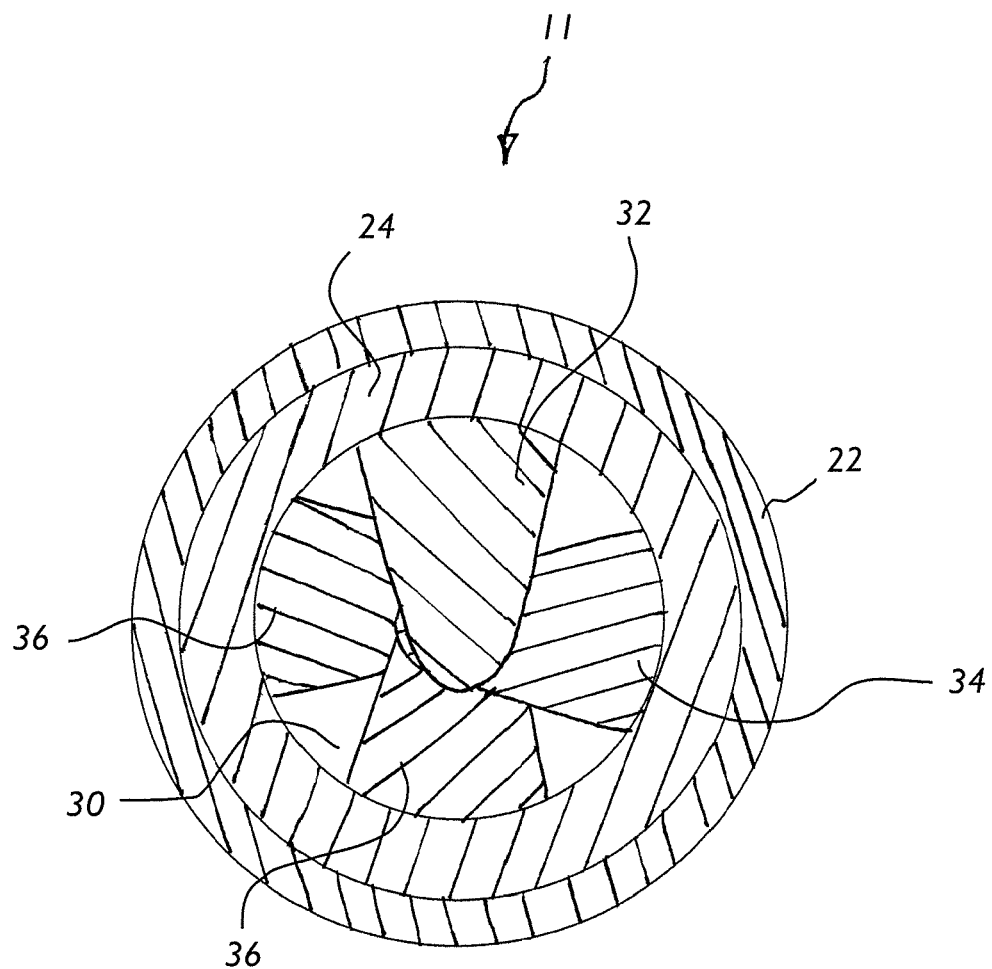
FIG. 3 is cross-sectional view of the cleaning system of FIG. 2 along line 3-3.

In some embodiments, the cleaning system (11) also includes one or more spacers (35) positioned between each of the plurality of the flexing flaps (32, 34, 36, 38). It should be noted that any number of cleaning members and/or spacers may be used in accordance with the present invention, depending on the desired length and application of the cleaning system (11). It is further understood that the shape of the flexing flaps (32, 34, 36, 38) illustrated in FIGS. 2 and 3 is only exemplary, and that any other shape may be used.

Figure 4:
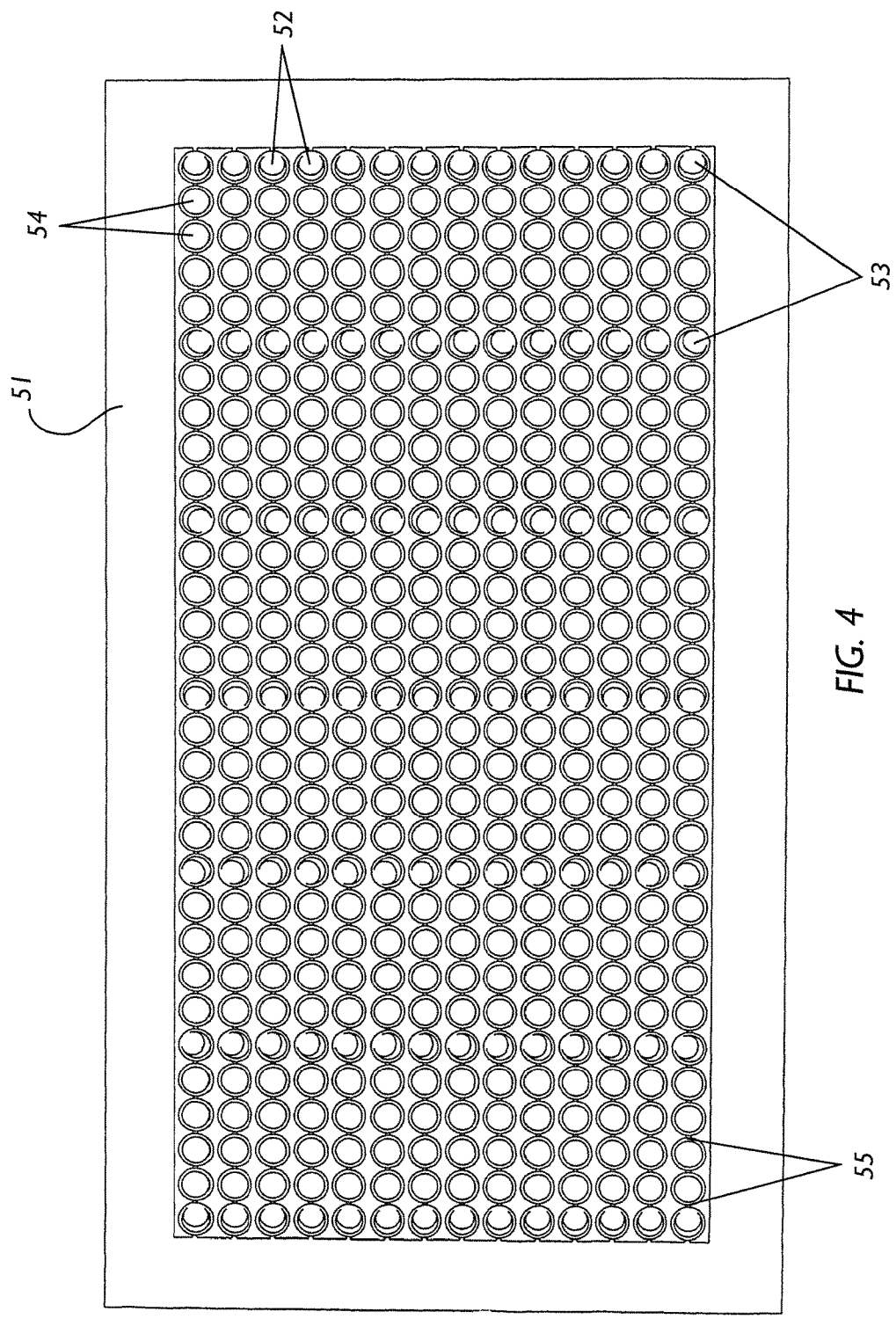
FIG. 4 illustrates a sheet of material from which a cleaning member of the cleaning system of FIG. 2 is produced.
Figure 5A:
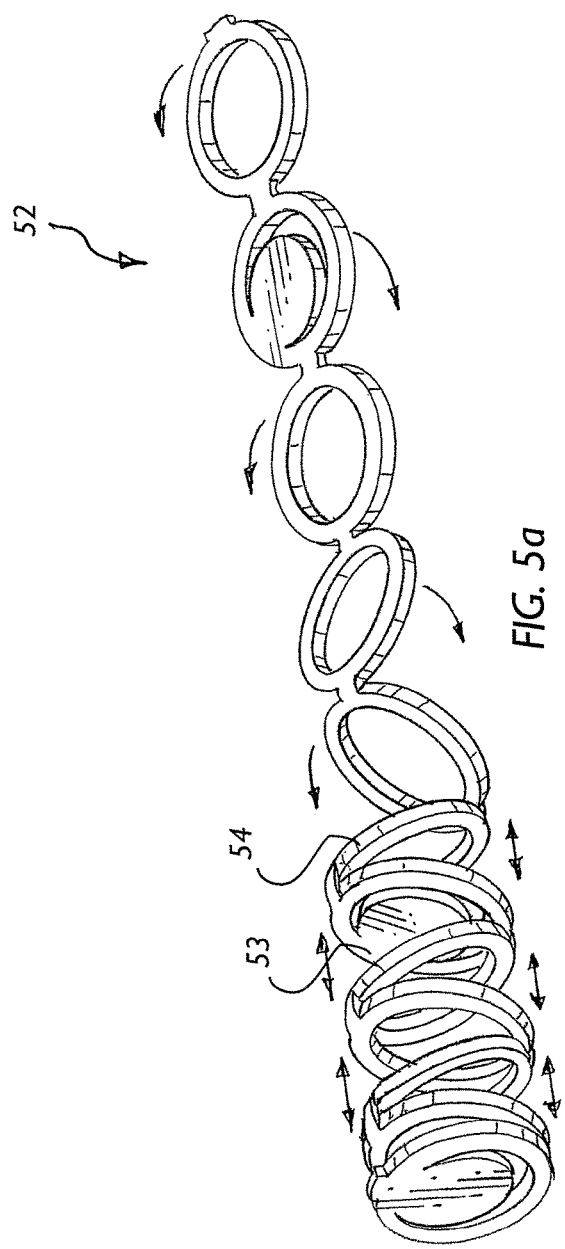
FIGS. 5a and 5b illustrate the process of making the cleaning member of the cleaning system of FIG. 2.
Figure 5B:
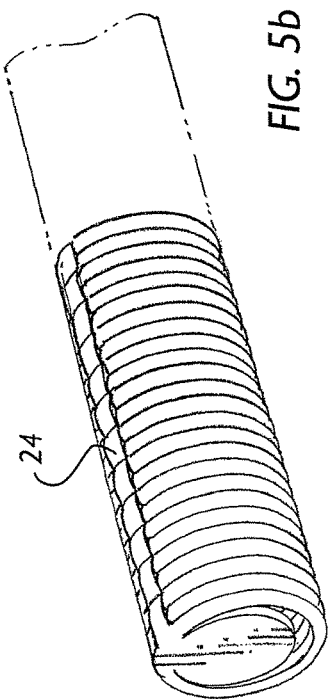

FIGS. 4, 5a and 5b illustrate one exemplary embodiment for making the cleaning member (24) of FIG. 2. As shown in FIG. 4, a sheet (51) of suitable flexible material, such as silicone, is used to produce a plurality of long strips (52). Each of the strips (52) contains a plurality of flexing flap members (53) separated by a plurality of spacer members (54). The flexing flap members (53) and the spacers (54) are connected by strips of material (55), such that a continuous strip of material is created. The strips (52) are cut from the sheet of material (51) by any suitable cutting technique, such as laser etching. The size and shape of the sheet (51) is chosen depending on desired shape, number and length of the strips (52). The sheet (51) may be of any suitable thickness, depending on desired thickness of the flexing flap members and spacer members. It is understood that the number and shape of the flexing flap members and spacers shown in FIG. 4 is only exemplary and that any other shapes and/or numbers may be used in accordance with the present invention.

Once the strips (52) are cut from the sheet of material (51), each strip is folded, as shown in FIG. 5a. Specifically, each of the members (53, 54) is folded onto the adjacent member, such that the strip (51) folds like an accordion. As a result, tubular cleaning member (24) is formed, as shown in FIG. 5b, consisting of flexing flap members separated by a plurality of spacers.

Figure 6:
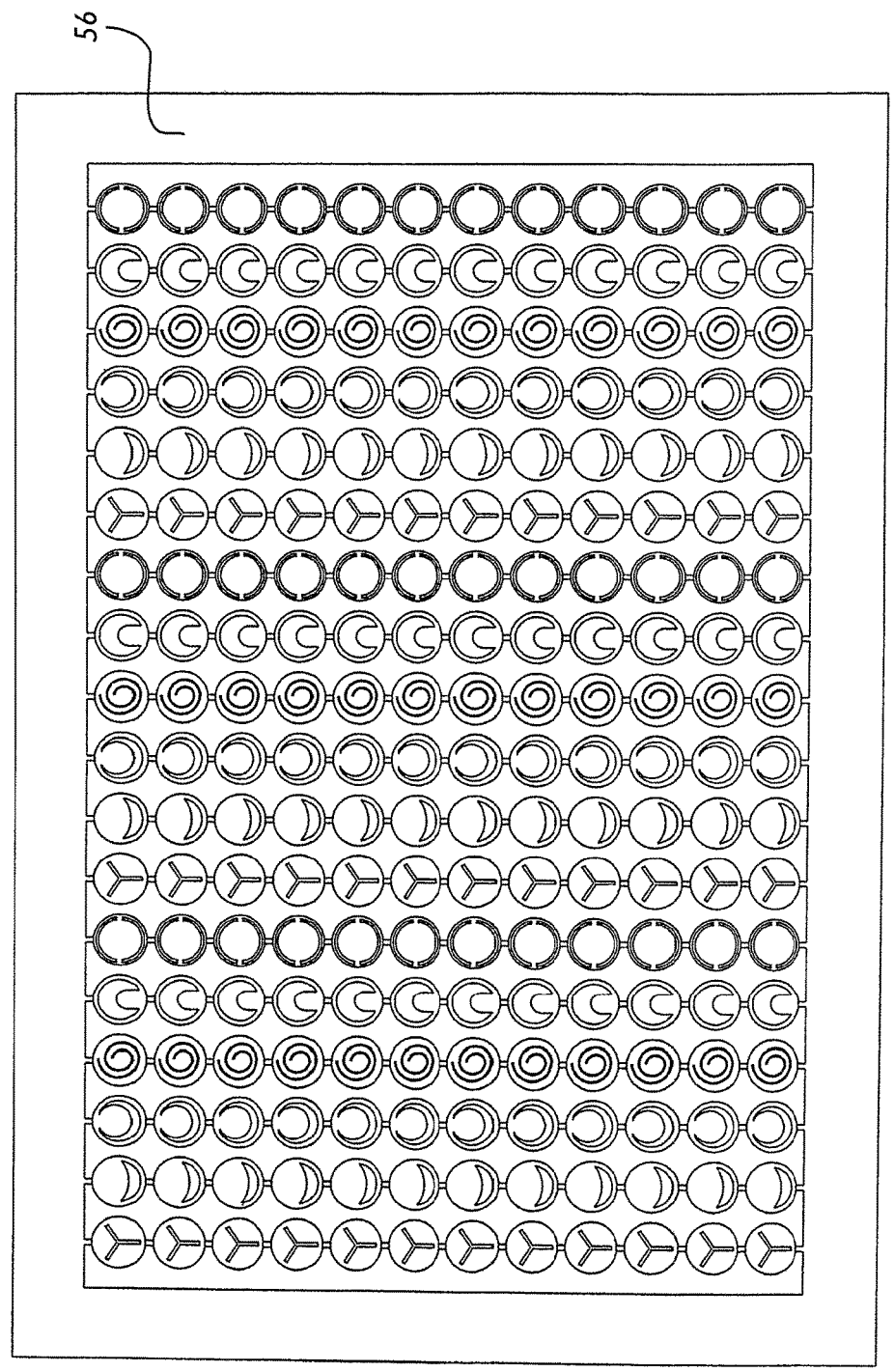
FIG. 6 illustrates a sheet of material from which the cleaning members for the cleaning system of FIG. 1 are produced.

The cleaning member may be comprised of flexing members of any suitable shape. For example, FIG. 6 illustrates other possible shapes of the flexing members that are cut out of a sheet of material (56). The flexing members (57) are cut as long strips (58) and then folded into tubular cleaning members, as shown in FIGS. 5a and 5b to be inserted into the cleaning system housing. In some embodiments, the strips (58) consist of a plurality of flexing members of the same type. In other embodiments, the strips (58) may include flexing members of different shapes. The flexing members may be connected in sequence or may be separated by spacers.

Figure 7:
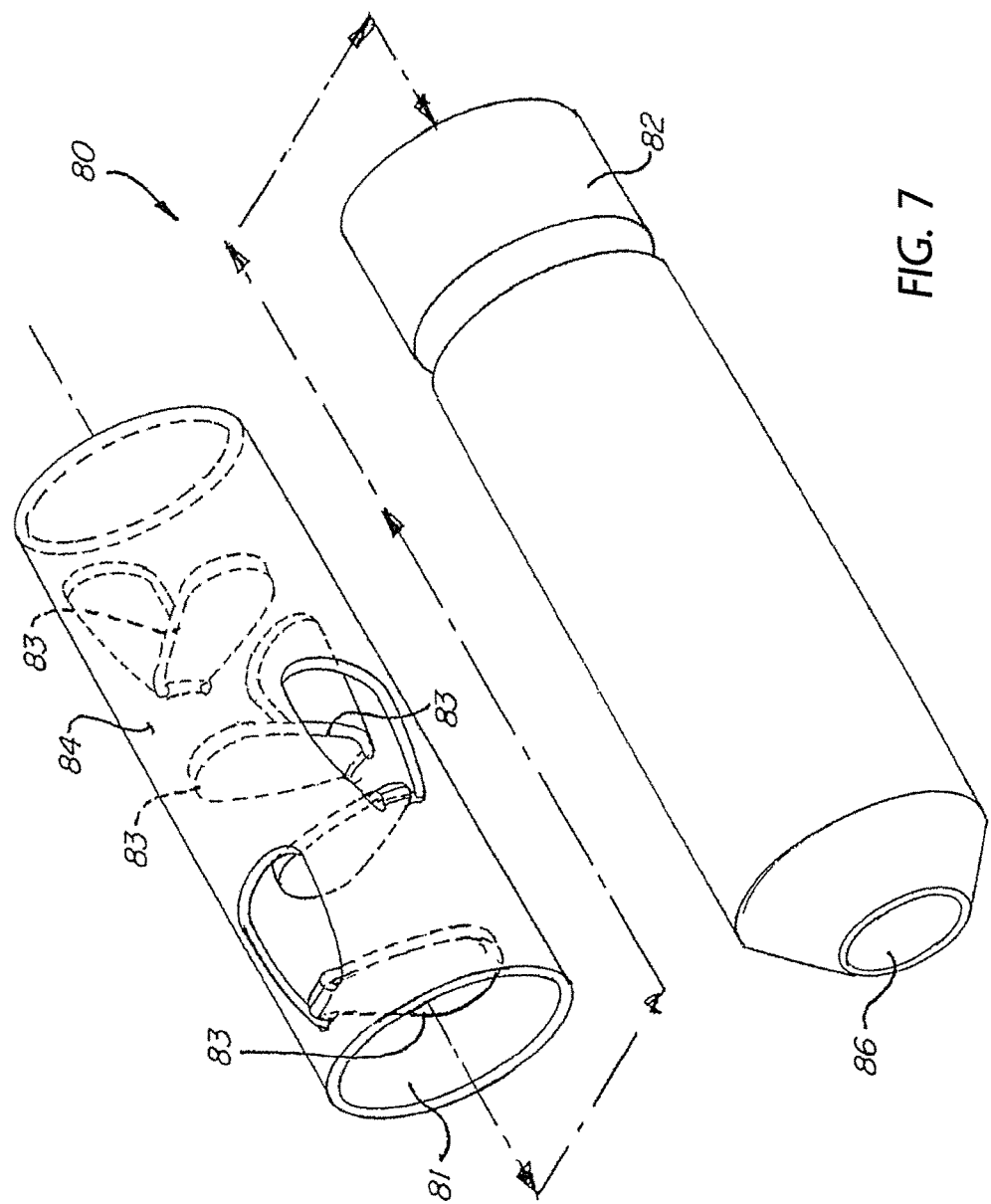
FIG. 7 is an enlarged schematic view of the cleaning system of FIG. 1.

FIG. 7 illustrates an additional embodiment of the cleaning system. As shown this figure, the cleaning system (80) including an outer housing (82) and a cleaning member (84) disposed inside the outer housing (82). The housing (82) has an opening (86) at its distal end, which is connected to a conduit (81) provided in the cleaning member (84), which in turn is connected with the lumen of the catheter. The cleaning member (84) may be attached to the outer housing (82) by any suitable means, such as by gluing it to the inner wall of the housing.

The cleaning member (84) has a tubular shape and may be made with any suitable flexible material, such as silicone. The cleaning member (84) includes a plurality of flexing flaps (83). The flexing flaps (83) are produced by cutting the flap shapes in the wall of the tubular cleaning member (84) by any suitable cutting technique, such as laser etching. Although the embodiment shown in FIG. 7 has four flexing flaps, any number of flaps may be positioned along the length of the cleaning member (84). Additionally, it is understood that the flexing flaps (83) may be of any other suitable shape in addition to the shape shown in FIG. 7.

After the flaps (83) are cut out, they are bent inward, such that the flaps extend into the conduit (81) provided in the cleaning member (84). In some embodiments, the flexing flaps (83) are bent inward by exposing them to high temperature to make the material more susceptible to deformation, and then cooling down the material such that the flaps retain their bent shape. As a result, when the imaging device is moved through the conduit (81) of the cleaning member (84), it displaces at least some of the flexible material and any debris trapped on the lens of the imaging device are thereby wiped off and cleaned.

Figure 8:
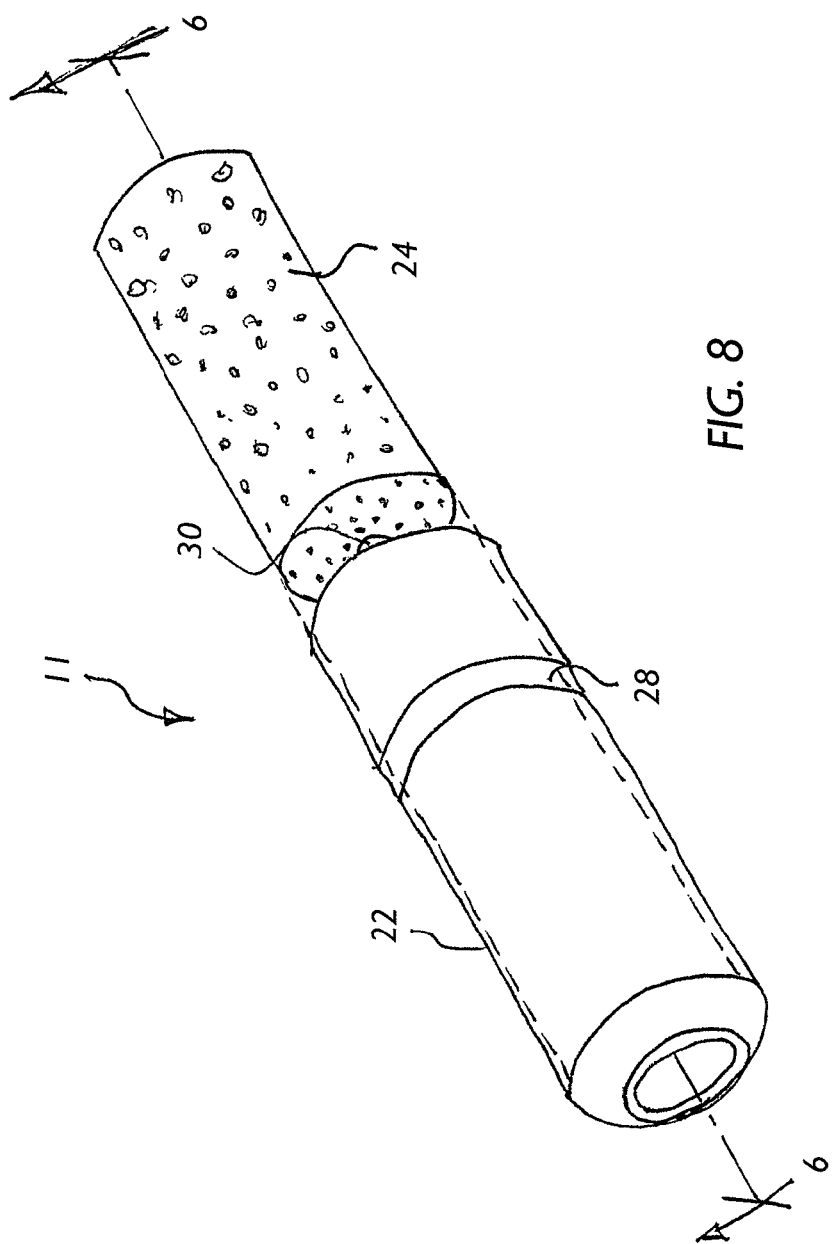
FIG. 8 is an enlarged schematic view of the cleaning system of FIG. 1.
Figure 9:
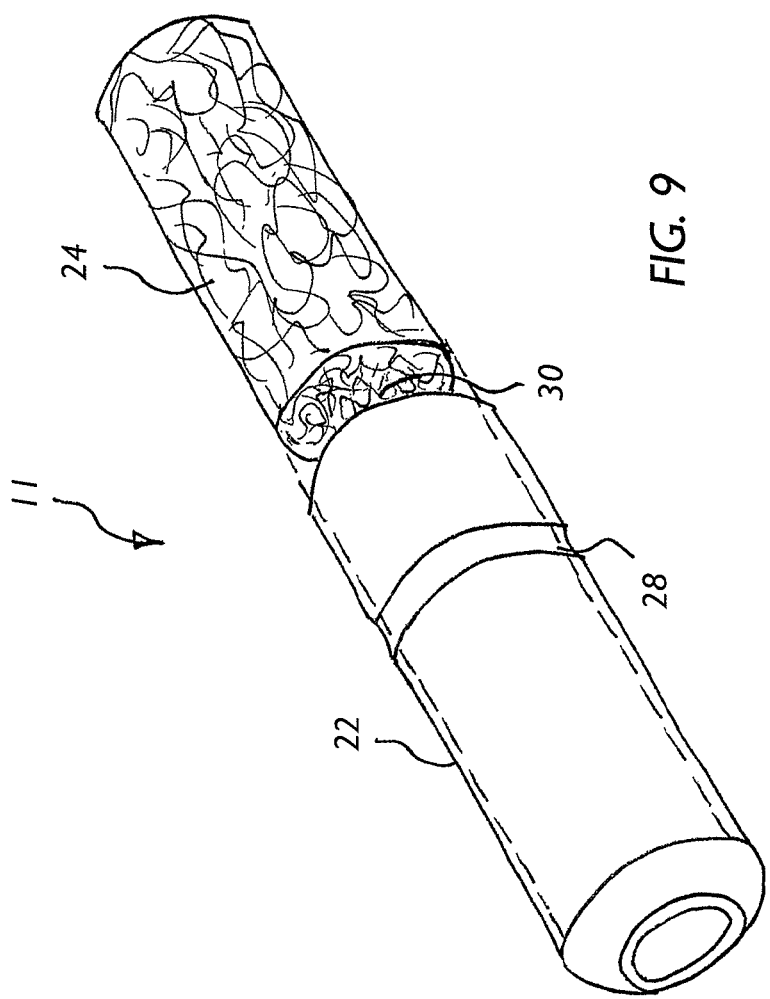
FIG. 9 is an enlarged schematic view of the cleaning system of FIG. 1.

FIGS. 8 and 9 illustrate alternative embodiments of the cleaning system (11) of the present invention. As illustrated in FIG. 8, the cleaning member (24) may be a tubular piece of flexible porous material, such as a sponge. The porous material has a conduit (30) that extends through the entire length of the cleaning member (24). The sponge material is affixed to the outer housing (22) of the cleaning system (11) by any suitable means, such as, e.g., by gluing the material to the inner wall of the housing.

In other advantageous embodiments, such as the embodiment shown in FIG. 9, the cleaning member (24) includes fibrous material, such as yarn, that has been weaved under tension and then released such that the yarn tangles, creating a textile bundle. When the imaging device is moved through the bundle (24), some of the yarns in the bundle are displaced by the tip of the imaging device, which facilitates whipping and cleaning of the lens of the imaging device. In one advantageous embodiment, an elastic yarn is weaved onto a mandrel in a stretched condition under tension. Then, the mandrel is positioned inside the outer housing (22) and the ends of the yarn are secured to the housing wall. Next, the mandrel is removed from the outer housing (22) through the opening at the distal end, which causes the yarn material to return back to its unstretched condition. As a result, the yarn expands and tangles, creating a bundle.

It should be noted that any other suitable flexible material may be used for the cleaning member (24). In some embodiments, the cleaning members may be made of bio-degradable materials.

In some embodiments, the housing (22) of the cleaning system (11) further includes imaging markers (28), such as radio opaque rings, located throughout the length of, or at the distal tip of the housing (22). Such markers can be selected and appropriately positioned in order to reflect the relevant waves of various imaging modalities (e.g., x-ray) in order to allow the use of such modalities to assist with the precise positioning of the catheter inside the patient's body. Additionally, the radio opaque rings can serve to indicate the exact location of the housing (22) relative to the tip of the imaging device under fluoroscopy.

Figure 10:
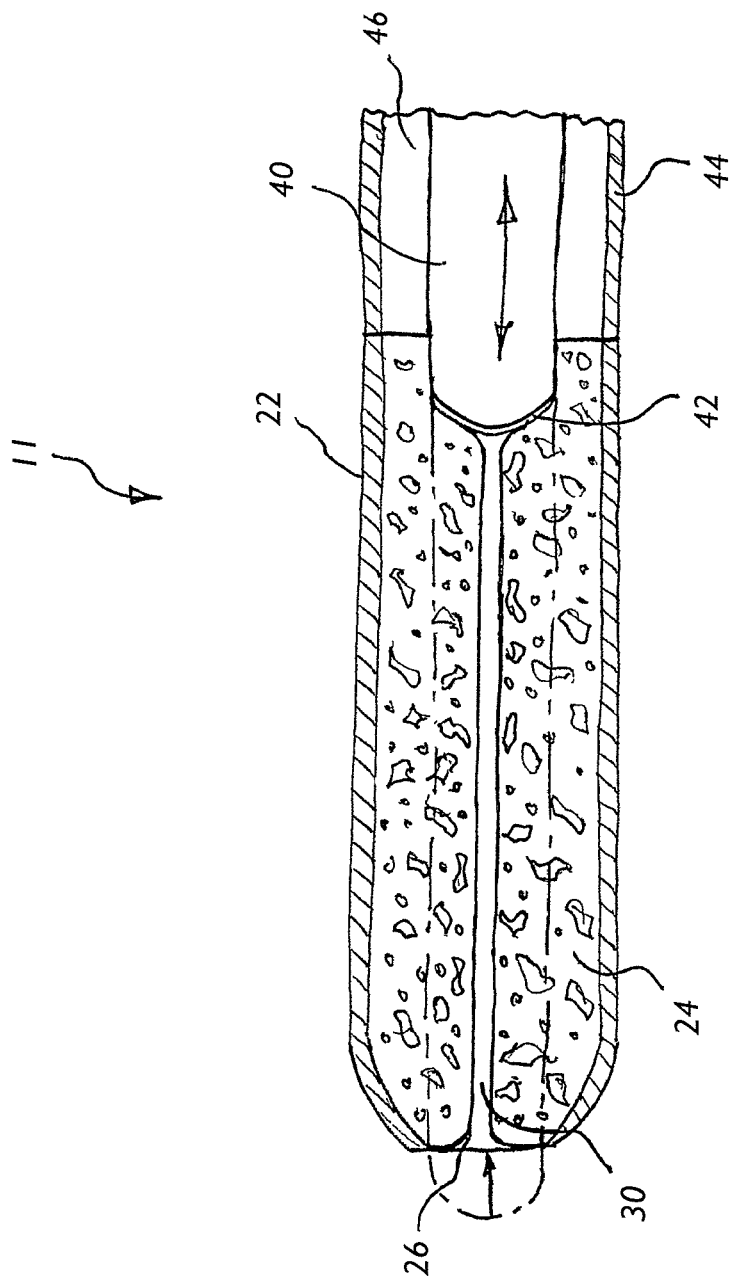
FIG. 10 is a cross-sectional view of the cleaning system of FIG. 8 along line 6-6, showing an imaging device movable therein.

The method of cleaning the imaging device lens in accordance with the invention is shown in FIG. 10. Before insertion of the imaging catheter (44) into a patient's body, the cleaning system (11) is attached to the distal end of the catheter. The imaging device (40) is inserted into the lumen (46) of the catheter, moved through the conduit (30) in the cleaning member (24), and then extended out of the opening (26) at the distal end of the housing (22) for visualizing the surrounding tissue. When the lens (42) of the imaging device (40) becomes fouled or fogged, the imaging device is cleaned by retracting the device back into the conduit (30) in the cleaning member (24) and then extending it back out of the distal end opening (26), as shown in FIG. 10. As the imaging device (40) is moved through the cleaning member (24), the distal tip of the imaging device pushes through the flexible material of the cleaning member (24), and any debris trapped on the lens (42) of the imaging device are wiped off by the cleaning member. The imaging device (40) may be actuated back and forth through the cleaning member (24) as many times as needed, until the lens is completely cleaned off.

Figure 11:
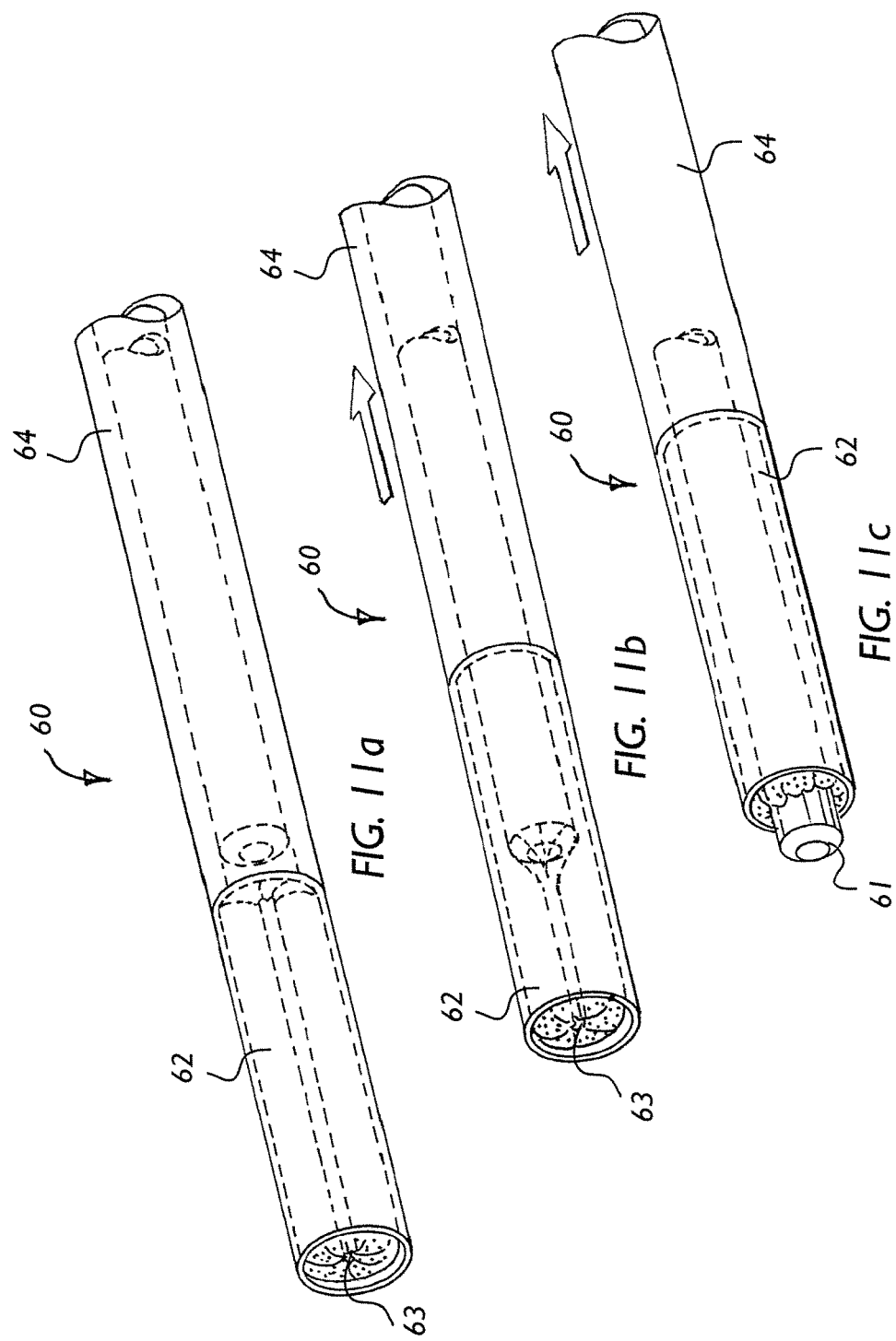
FIGS. 11a-11c are enlarged schematic views of the cleaning system of FIG. 1, showing an imaging device being actuated through the cleaning member.

FIGS. 11a-11c illustrate another embodiment of the method of cleaning the imaging device lens in accordance with the invention. In this embodiment, the cleaning system (60) includes a cleaning member (62) connected to an elongated sleeve (64). The cleaning member (62) is positioned at a distal end of an imaging device (61), such as an endoscope, and the sleeve (64) is slid over the imaging device, as shown in FIG. 11a. The sleeve is made out of any biocompatible material that is flexible enough such that it can be used with flexible endoscope and catheters. The cleaning member (62) has a conduit terminating at an opening (63) at a distal end of the cleaning member, such that the imaging device (61) is extended through the conduit and out of the opening (63). Similarly to the other embodiments described above, the cleaning member (62) includes a flexible material at least partially occluding the conduit, such that the imaging device displaces at least some of the flexible material when it moves through the conduit, thereby cleaning the lens of the imaging device, as illustrated in FIGS. 11b and 11c.

In the embodiment shown in FIGS. 11a-11c, the cleaning member (62) is moved relative to the imaging device (61) by actuating the sleeve (64) at its proximal end, which is positioned outside the patient's body. Such design is advantageous when the imaging device is precisely positioned at the target tissue site, and it is undesirable to move the imaging device to clean the lens. Additionally, because the cleaning member with the attached sleeve is provided as a separate piece that is moved over the imaging device, the cleaning system (60) may be used with any type of an existing medical imaging device.

Figure 12:
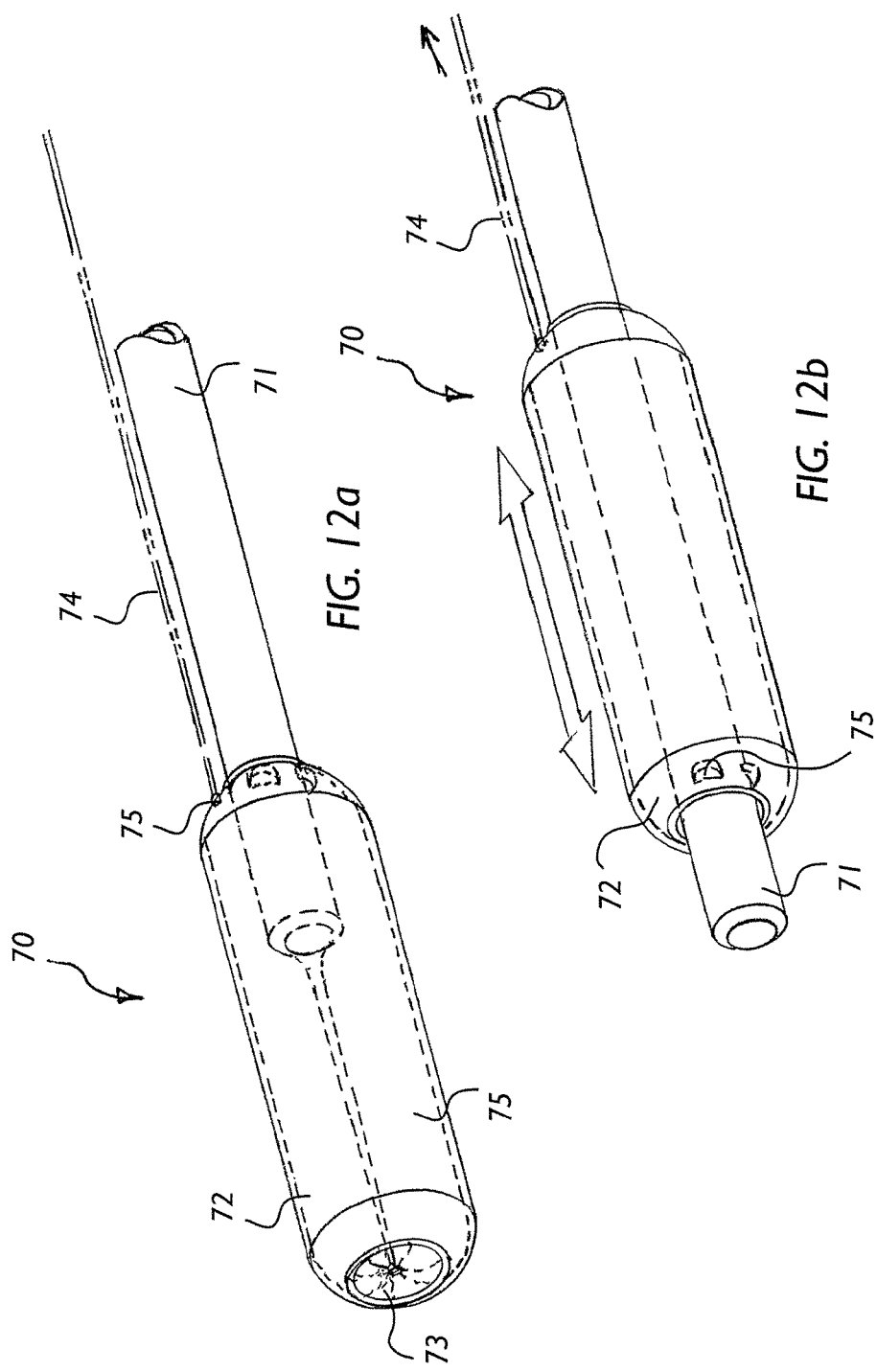
FIGS. 12a and 12b are enlarged schematic views of the cleaning system of FIG. 1, showing an imaging device being actuated through the cleaning member.

Yet another embodiment of the cleaning system in accordance with the present invention is shown in FIGS. 12a and 12b. In this embodiment, the cleaning system (70) includes a cleaning member (72) movably disposed at a distal end of an imaging device (71), such as an endoscope, as shown in FIG. 12a. The cleaning member (72) is connected to an actuation mechanism (74), such as a pull wire, that can be actuated by a surgeon from outside of the patient's body. The cleaning member (72) has an opening (73) at its distal end and a conduit through which the imaging device (71) is moved. In some advantageous embodiments, the imaging device (71) includes at least one stop member (75) provided on the outer wall of the imaging device. The stop member (75) functions to limit the movement of the cleaning member (72) beyond two end positions, as shown in FIGS. 12a and 12b. In is understood that any other stop feature may be utilized to constrain the movement of the cleaning member (72) in accordance with the present invention.

When in use, the cleaning member (72) is moved by the actuation mechanism (74) back and forth relative to the imaging device (71), as illustrated in FIGS. 12a and 12b. As a result, a flexible material (75) at least partially occluding the conduit of the cleaning member (72) is displaced by a distal end of the imaging device, thereby cleaning the lens of the imaging device.

In some embodiments, the cleaning members (24) may be made of different colors (i.e. red, green, blue) or textures such that the user can directly visualize the location of the imaging device tip as it is moved forward and back through the cleaning members (24) and observe the cleaning status.

In some advantageous embodiments, a cleansing solution is used to further assist in cleaning the lens of the imaging device (40). Any suitable cleansing solution, such as saline solution, glycol solution, alcohol solution, water, any combination thereof, or any other biocompatible fluid may be used in accordance with the present invention. In some embodiments, the cleansing solution is supplied though the same catheter lumen (46) as the lumen used to introduce the imaging device (40) into the bodily cavity. In other embodiments, a separate catheter lumen may be used to supply the cleansing solution to the cleaning system (11). The cleansing solution is used to saturate the cleaning member (24) to enhance the cleaning of the imaging device. Additionally, the cleansing solution may be provided to the housing (22) of the cleaning system (11) to rinse the imaging device as it is moved through the cleaning member (24).

The cleansing solution may be supplied via a syringe or via any other fluid introduction device. The fluid introduction device may be coupled to a Y-junction provided at a distal end of the catheter shaft. After the imaging device lens is rinsed by the cleansing solution, the solution is suctioned out through one of the catheter lumens via a syringe or any other suitable suction device. Other cleansing media, such as, e.g., pressurized air, may also be used in conjunction with the cleaning member.

Figure 13:
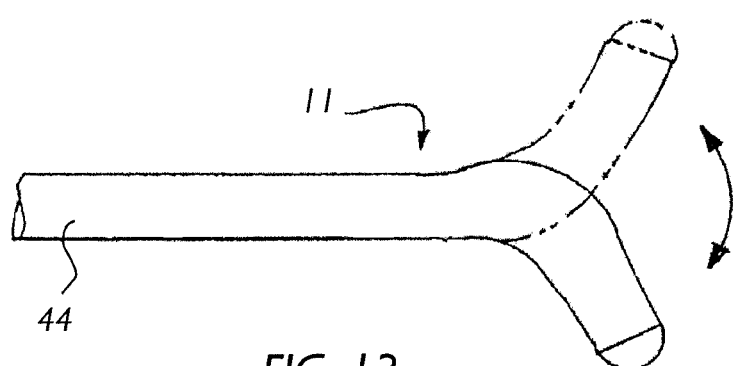
FIG. 13 is a schematic view of the imaging catheter device with the cleaning system of FIG. 1, showing flexible positions of the distal tip.

In some embodiments, the cleaning system is also used as a safety tip for the distal end of the catheter to facilitate safe insertion of the catheter into a patient's body. As shown in FIG. 13, the cleaning system (11) is attached to the distal end of the catheter (44). Because the housing and the cleaning member of the cleaning system (11) are made out of flexible material, e.g. silicone, sponge or yarn, as described above, the cleaning system (11) is capable of bending when it meets an obstacle, such as tissue wall. When the catheter (44) is introduced in a bodily cavity, the cleaning system (11) at the distal end deflects away from tissue and organ walls without damaging them, thus ensuring a safe insertion of the catheter.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:
1. An imaging catheter device comprising:
   a catheter body having a proximal end, a distal end, and a lumen extending in a longitudinal direction;
   a cleaning member disposed at the distal end of said catheter body; and
   an imaging device movably disposed in said lumen and through said cleaning member;

wherein said cleaning member includes a conduit through which said imaging device moves;

wherein said cleaning member further includes a plurality of flexing flaps at least partially occluding the conduit such that said imaging device displaces at least some of the flexing flaps when moved through the conduit to clean said imaging device; and wherein at least one of the flexing flaps is not aligned in the longitudinal direction with at least one other flexing flap.

2. The imaging catheter device of claim 1, wherein said cleaning member is movable relative to the imaging device.

3. The imaging catheter device of claim 1, wherein the imaging device is movable relative to said cleaning member.

4. The imaging catheter device of claim 1, further comprising a fluid supplied to said cleaning member via the lumen of said catheter body.

5. The imaging catheter device of claim 1, wherein said cleaning member is disposable and is removably attached to the distal end of said catheter body.

6. A cleaning system for a medical imaging device, comprising:

a housing for positioning at a distal end of the imaging device; and a cleaning member disposed in said housing;

wherein said cleaning member comprises:

a conduit extending in a longitudinal direction, through which the imaging device moves; and a plurality of flexing flaps at least partially occluding the conduit such that the imaging device displaces at least some of the flexing flaps when moved through the conduit;

wherein at least one of the flexing flaps is not aligned in the longitudinal direction with at least one other flexing flap.

7. The cleaning system of claim 6, wherein the plurality of flexing flaps comprise silicone material.

8. The cleaning system of claim 6, wherein the plurality of flexing flaps comprise fabric material.

9. The cleaning system of claim 6, further comprising at least one spacer element positioned between adjacent flexing flaps.

10. The cleaning system of claim 6, wherein each of the plurality of flexing flaps has a different color or texture.

11. The cleaning system of claim 6, further comprising a fluid supplied to said housing.

12. The cleaning system of claim 11, wherein the fluid is saline.

13. The cleaning system of claim 11, wherein the fluid is alcohol.

14. The cleaning system of claim 11, further comprising a lumen for supplying the fluid to said housing.

15. The cleaning system of claim 14, wherein the lumen accommodates a fluid suctioned from said housing.

16. The cleaning system of claim 11, wherein said cleaning member is impregnated with the fluid.

17. The cleaning system of claim 16, wherein said cleaning member retains the fluid via surface tension.

18. The cleaning system of claim 6, wherein a distal end of said housing has a rounded shape.

19. The cleaning system of claim 6, wherein said housing comprises flexible material such that said housing deflects away from bodily structures in a patient's body.

20. The cleaning system of claim 6, further comprising a plurality of spacers, wherein each of the plurality of spacers is positioned between adjacent flexing flaps.

21. The cleaning system of claim 20, wherein two or more spacers are positioned between the adjacent flexing flaps.

22. A method of cleaning a medical imaging device, comprising the steps of:

positioning a cleaning member at a distal end of the medical imaging device, said cleaning member including a conduit extending in a longitudinal direction and a plurality of flexing flaps at least partially occluding the conduit, wherein least one of the flexing flaps is not aligned in the longitudinal direction with at least one other flexing flap; and cleaning the imaging device by moving at least one of the imaging device and the cleaning member relative to the other to move the imaging device through the conduit in said cleaning member such that the imaging device displaces at least some of the flexing flaps.

23. The method of claim 22, wherein said cleaning device is moved relative to the imaging device to move the imaging device through the conduit in said cleaning member.

24. The method of claim 22, wherein the imaging device is moved relative to said cleaning member to move the imaging device through the conduit in said cleaning member.

25. The method of claim 22, further comprising the step of supplying a fluid to said cleaning member via a lumen in the medical imaging device.

26. The method of claim 25, wherein the step of supplying fluid to said cleaning member further comprises impregnating the flexing flaps with the fluid.

27. The method of claim 22, further comprising the step of suctioning the fluid from said cleaning member via a lumen in the medical imaging device.

28. The method of claim 22, further comprising the step of supplying pressurized air to said cleaning member.

29. The method of claim 22, further comprising repeating the step of moving the imaging device through the conduit in said cleaning member.

* * * * *